United States Patent [19]

Baughn et al.

[11] 4,024,268

[45] May 17, 1977

[54] USE OF AMPICILLIN FOR THE TREATMENT OF SWINE DYSENTERY

[75] Inventors: Charles O. Baughn, Flemington, N.J.; Wayne H. Linkenheimer, Washington Crossing, Pa.; William E. Brown, Princeton, N.J.

[73] Assignee: E. R. Squibb & Sons, Inc., Princeton, N.J.

[22] Filed: Mar. 18, 1976

[21] Appl. No.: 668,005

[52] U.S. Cl. .............................................. 424/271
[51] Int. Cl.² ...................................... A61K 31/43
[58] Field of Search ................................... 424/271

[56] References Cited
OTHER PUBLICATIONS

Ustimenko et al., Chem. Abst., vol. 77, (1972), p. 70733e.

Primary Examiner—Sam Rosen
Attorney, Agent, or Firm—Lawrence S. Levinson; Merle J. Smith; Donald J. Barrack

[57] ABSTRACT

Swine dysentery can be treated by the oral administration to swine suffering from the disease of an effective amount of ampicillin.

5 Claims, No Drawings

USE OF AMPICILLIN FOR THE TREATMENT OF SWINE DYSENTERY

BACKGROUND OF THE INVENTION

Swine dysentery is a mucohemorrhagic, diarrheal disease that affects primarily weanling pigs, but may affect larger pigs. The disease is often referred to as bloody scours, bloody dynsentery, hemorrhagic dysentery, mucohemorrhagic diarrhea, or vibrionic dysentery. The disease occurs in many swine-raising areas of the world.

Morbidity is usually greater than 90% in weanling pigs and mortality may reach 75%. Experimentally, swine dysentery may decrease the rate of weight gain two fold and decrease efficiency of feed conversion threefold, as compared with uninfected control pigs. The disease causes tremendous financial losses because of death and decreased rate of growth of infected swine.

The cause of swine dysentery is, as yet, ill defined. In the past, *Vibrio coli* has been associated with the disease. More recently, a large spirochete *Treponema hyodysenteriae*, acting in association with other intestinal microorganisms, is thought to be the cause of the disease. At present, the only reliable method of experimental reproduction of the disease is to inoculate susceptible pigs with colonic mucosa and colonic contents of pigs acutely affected with the disease.

The outlook for successful prevention and control of swine dysentery has not been promising because no product previously approved for use in the United States has completely prevented recurrence of the disease. Many swine owners have ultimately had to depopulate, clean, disinfect and restock when the disease became enzootic. It appears that any immunity that develops from natural infection is short lived, and little optimism is expressed concerning the early development of a useful immunologic agent or vaccine.

SUMMARY OF THE INVENTION

It is an object of this invention to provide an effective method of treating swine dysentery.

It is a further object of this invention to treat swine dysentery by the oral administration of an agent that can be added to the swine's feed or the swine's drinking water.

These and other objects, that will be readily apparent to a person or ordinary skill in the art, are realized by the method of this invention. The method of this invention comprises orally administering to swine infected with swine dysentery an effective amount of ampicillin.

DETAILED DESCRIPTION OF THE INVENTION

Swine can be effectively treated for swine dysentery by the oral administration of ampicillin. For the treatment of swine dysentery, ampicillin can be administered to a swine in an amount of from about 0.5 milligrams/kilogram of animal body weight/day to 55 milligrams/kilogram of animal body weight/day, preferably about 10 milligrams/kilograms of animal body weight/day to 15 milligrams/kilogram of animal body weight-day.

Ampicillin (D-(2-amino-2-phenylacetamido)-3,3-dimethyl-7-oxo-4-thia-1-azabicyclo[3.2.0]heptane-2-carboxylic acid) is a synthetic penicillin having the formula

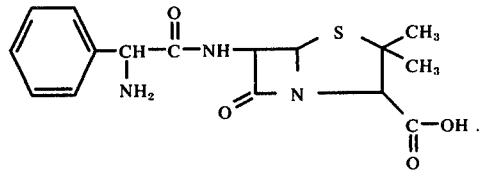

As disclosed in U.S. Pat. No. 2,985,648 issued on May 23, 1961, ampicillin belongs to a class of compounds which are "of value as antibacterial agents, as nutritional supplements in animal feeds, as agents for the treatment of mastitis in cattle and as therapeutic agents in poultry and animals, including man, in the treatment especially of diseases caused by Gram-positive and Gram-negative bacteria...."

Ampicillin for the treatment of swine dysentery can be administered orally to a swine infected with the disease in the form of a tablet, capsule, powder, or the like. To facilitate treatment of the animals, it is preferred that ampicillin be administered in the feed or drinking water of the swine. Since swine suffering from swine dysentery often do not eat, administration of ampicillin in the drinking water is most preferred.

The following examples demonstrate the effectiveness of ampicillin in treating swine dysentery.

EXAMPLE

Thirty male and female pigs, 4 to 6 weeks of age, are conditioned for 3 days to accept cows' milk. The pigs are weighed and identified and six uninfected pigs to be used as a control are removed. The remaining 24 pigs are infected orally by the addition to their milk of colonic scrapings from a pig which has been acutely infected with swine dysentery.

When signs of swine dysentery are present in the majority of the pigs, the infected pigs are weighed and randomly assigned to treatment groups (six pigs per group), and treatment is started. The five groups of pigs are broken down as follows:

1. Uninfected control group.
2. Infected control group.
3. Group treated with tylosin at a concentration of 0.0066% in the drinking water.
4. Group treated with ampicillin at a concentration of 0.00882% in the drinking water.
5. Group treated with ampicillin at a concentration of 0.00441% in the drinking water.

The pigs are weighed again on the 6th day of infection, one day after the end of treatment. The presence of *T. hyodysenteriae* is determined by rectal swabs.

The results are set forth in Table I below. The data show that the uninfected control group which received no treatment had a mean weight gain of 1.19 kilograms. The group that was infected but had no treatment experienced a mean weight loss of 0.77 kilograms. All six pigs remained infected at the end of the test. The group treated with tylosin experienced a mean weight loss of 0.31 kilograms and at the end of the treatment four out of the six pigs still harbored *T. hyodysenteriae*. The group treated with ampicillin at a concentration of 0.00882% experienced a mean weight gain of 1.96 kilograms and none of the pigs harbored *T. hyodysenteriae* at the end of the test. The group treated with ampicilin at the lower concentration experienced a mean weight gain of 0.69 kilograms and three of the six pigs no longer harbored T. hyodysenteriae.

It should be noted that the group treated with tylosin at a concentration of 0.0066% did not respond to treatment as well as the group treated with ampicillin at a concentration of 0.00441%. Tylosin is an antibiotic used to fight infections in swine.

milligrams per kilogram of animal body weight per day to 55 milligrams per kilogram of animal body weight per day.

3. A method in accordance with claim 1 wherein the ampicillin is administered in an amount of from 10 milligrams per kilogram of animal body weight per day to 15 milligrams per kilogram of animal body weight per day.

4. A method in accordance with claim 1 which comprises first combining ampicillin with the swine's feed.

5. A method in accordance with claim 1 which comprises first combining ampicillin with the swine's drinking water.

TABLE 1

| Treatment | Pig No. | starting weight | weight after infection | weight gain during infection | Diarrhea at start of treatment | presence of T. hyodysenteriae at start of treatment | weight after treatment | weight gain during treatment | presence of T. hyodysenteriae after treatment |
|---|---|---|---|---|---|---|---|---|---|
| | 20 | 8.20 | 9.77 | 1.57 | —* | — | 11.22 | 1.45 | — |
| | 34 | 6.63 | 7.54 | .91 | — | — | 7.85 | .31 | — |
| No infection | 35 | 7.42 | 9.77 | 2.35 | — | — | 11.83 | 2.06 | — |
| | 55 | 8.02 | 9.37 | 1.35 | — | — | 11.29 | 1.92 | — |
| No treatment | 57 | 7.80 | 7.62 | −.18 | — | — | 7.07 | −.55 | + |
| | 64 | 5.40 | 6.67 | 1.27 | — | — | 8.66 | 1.99 | — |
| | mean | 7.25 | 8.46 | 1.21 | | | 9.65 | 1.19 | |
| | 29 | 5.25 | 4.53 | −.72 | +** | + | 3.78 | −.75 | + |
| | 32 | 6.58 | 7.61 | 1.03 | + | — | 6.32 | −1.29 | + |
| Infected; | 33 | 7.83 | 6.90 | −.93 | + | + | 6.43 | −.47 | + |
| | 50 | 7.56 | 6.65 | −.91 | + | + | 6.16 | −.49 | + |
| No treatment | 56 | 6.31 | 5.37 | −.94 | + | + | 4.47 | −.90 | + |
| | 65 | 5.78 | 4.60 | −1.18 | + | + | 3.87 | −.73 | + |
| | mean | 6.55 | 5.94 | −.61 | | | 5.17 | −.77 | |
| | 15 | 6.75 | 7.01 | .26 | + | + | 8.50 | 1.49 | — |
| | 18 | 8.02 | 6.92 | −1.10 | + | + | 6.46 | −.46 | + |
| Infected; | 30 | 6.61 | 5.55 | −1.06 | + | + | 4.60 | −.95 | + |
| treatment | 39 | 7.23 | 6.54 | −.69 | + | + | 6.21 | −.33 | + |
| with Tylosin | 41 | 8.80 | 8.61 | −.18 | + | — | 8.75 | .13 | — |
| 0.0066% | 61 | 8.30 | 9.07 | +.77 | + | + | 7.33 | −1.74 | + |
| | mean | 7.62 | 7.29 | −.33 | | | 6.98 | −.31 | |
| | 25 | 7.95 | 8.16 | .21 | + | + | 9.95 | 1.79 | — |
| Infected; | 28 | 8.58 | 7.86 | −.72 | + | + | 10.41 | 2.55 | — |
| treatment | 37 | 6.06 | 5.10 | −.92 | + | + | 7.31 | 2.22 | — |
| with | 43 | 7.69 | 7.68 | −.01 | + | + | 9.49 | 1.81 | — |
| Ampicillin *** | 62 | 6.16 | 7.20 | 1.04 | + | + | 9.09 | 1.89 | — |
| 0.00882% | 66 | 6.20 | 5.76 | −.44 | + | + | 7.23 | 1.47 | — |
| | mean | 7.11 | 6.96 | −.15 | | | 8.91 | 1.96 | |
| | 16 | 8.78 | 7.10 | −1.68 | + | + | 6.11 | −.99 | + |
| | 38 | 7.25 | 6.54 | −.66 | + | + | 9.02 | 2.43 | — |
| Infected; | 42 | 4.65 | 5.96 | 1.31 | + | — | 8.28 | 2.32 | — |
| treatment | 46 | 6.03 | 5.50 | −.53 | + | + | 4.59 | −.91 | + |
| with | 52 | 4.20 | 6.30 | 2.10 | + | — | 8.59 | 2.29 | — |
| Ampicillin | 53 | 8.39 | 6.39 | −2.00 | + | + | 5.39 | −1.00 | + |
| 0.00441% | mean | 6.55 | 6.31 | −.24 | | | 7.00 | .69 | |

* In this table "−" indicates negative
** In this table "+" indicates positive
*** Ampicillin is utilized in the form of the trihydrate.

What is claimed is:

1. A method for treating swine dysentery which comprises orally administering to a swine infected with *Treponema hyodysenteriae* an effective amount of ampicillin.

2. A method in accordance with claim 1 wherein the ampicillin is administered in an amount of from 0.5